US007502712B2

(12) United States Patent
Mateo Martinez

(10) Patent No.: US 7,502,712 B2
(45) Date of Patent: Mar. 10, 2009

(54) PREVENTIVE DEFECT DETECTION AND CONTROL PROCESS IN COMPOSITE MATERIAL PARTS

(75) Inventor: Antonio Maria Mateo Martinez, Valladolid (ES)

(73) Assignee: Airbus Espana S.L., Madrid (ES)

( * ) Notice: Subject to any disclaimer, the term of this patent is extended or adjusted under 35 U.S.C. 154(b) by 300 days.

(21) Appl. No.: 11/206,661

(22) Filed: Aug. 18, 2005

(65) Prior Publication Data

US 2006/0287836 A1 Dec. 21, 2006

(30) Foreign Application Priority Data

Jun. 20, 2005 (WO) ................ PCT/ES2005/070094

(51) Int. Cl.
*G06F 17/18* (2006.01)
*G06F 19/00* (2006.01)

(52) U.S. Cl. ......................... 702/179; 702/35; 702/185; 702/190; 73/611; 73/620; 367/95; 367/197; 382/149

(58) Field of Classification Search ................... 702/35, 702/179, 181, 183, 185, 190; 73/611, 614, 73/615, 616, 620; 367/95, 197; 382/149
See application file for complete search history.

(56) References Cited

U.S. PATENT DOCUMENTS

| | | | | |
|---|---|---|---|---|
| 4,674,334 | A * | 6/1987 | Chimenti et al. | 73/627 |
| 5,343,750 | A * | 9/1994 | Bashyam | 73/635 |
| 5,404,754 | A * | 4/1995 | Wang | 73/602 |
| 5,445,029 | A * | 8/1995 | Falsetti et al. | 73/609 |
| 5,476,010 | A * | 12/1995 | Fleming et al. | 73/620 |
| 6,089,095 | A * | 7/2000 | Yang et al. | 73/600 |
| 6,128,092 | A * | 10/2000 | Levesque et al. | 356/451 |
| 6,494,098 | B1 * | 12/2002 | Leybovich | 73/620 |
| 6,606,909 | B2 * | 8/2003 | Dubois et al. | 73/600 |
| 7,006,878 | B2 * | 2/2006 | Schweizerhof et al. | 700/51 |

* cited by examiner

*Primary Examiner*—Edward Raymond
*Assistant Examiner*—Elias Desta
(74) *Attorney, Agent, or Firm*—Ladas and Parry LLP

(57) ABSTRACT

A preventive defect detection and control process for a mass produced composite material parts automatically obtains representative parameters of backwall and intermediate echo signal results in each cell of a mesh predefined on the parts, stores the parameters in a database and statistically analyzes the stored parameters for detecting isolated and significant alterations in the parts manufacturing process generating porosity defects, detecting slow and permanent alterations in the parts manufacturing process generating porosity defects or detecting areas with a negligible defect generation probability in order to identify areas susceptible of inspection by sampling.

16 Claims, 7 Drawing Sheets

DATA ACQUISITION — 100
STORAGE — 110
120
130 — ISOLATED ALTERATION ANALYSYS
PREVENTIVE BEHAVIOUR — SI — PREVENTIVE ACTION
NO
140 — PERMANENT ALTERATION ANALYSIS
PREVENTIVE BEHAVIOUR — SI — PREVENTIVE ACTION
NO
150 — CAPABILITY ANALYSIS
CAPABLE PROCESS — SI — INSPECTION REDUCTION

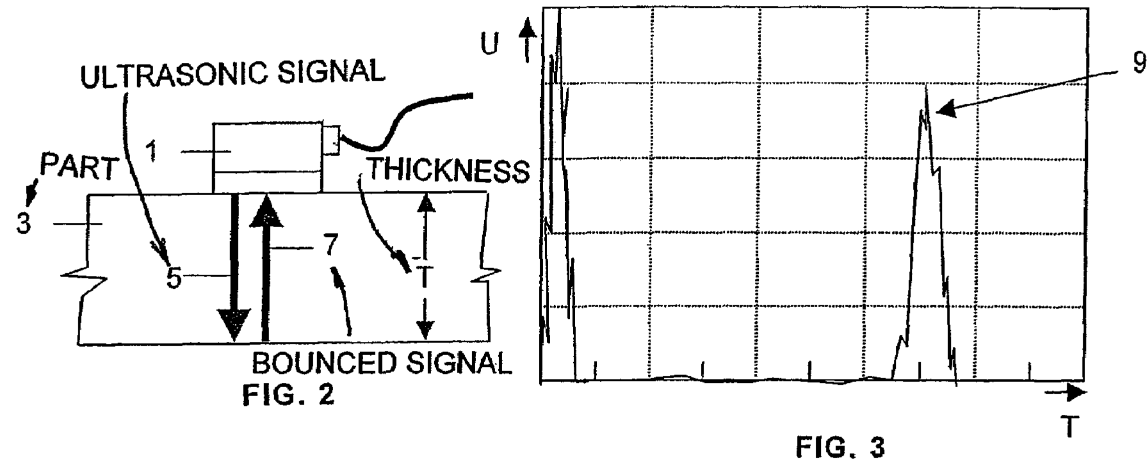
FIG. 2
FIG. 3
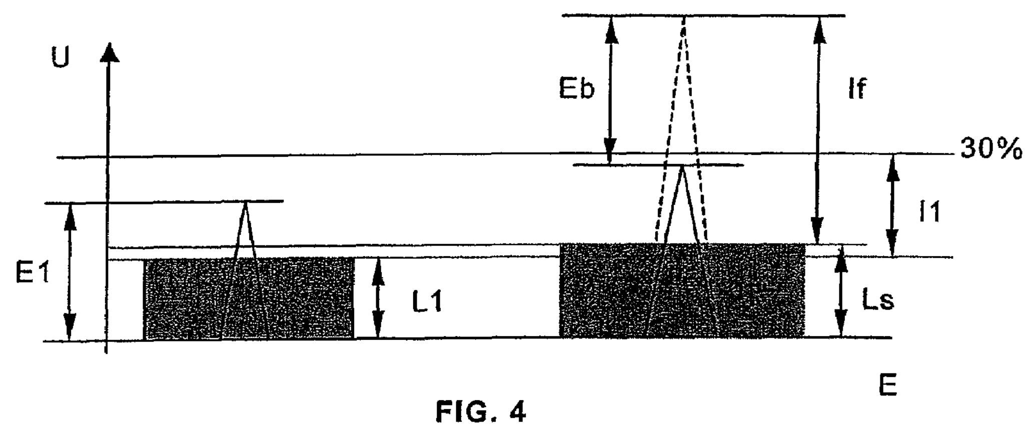
FIG. 4
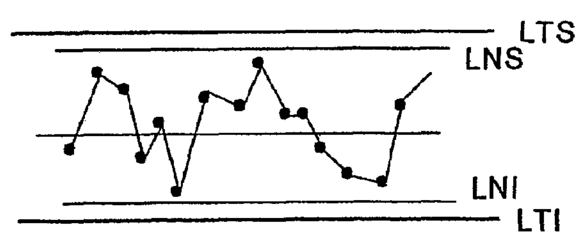
FIG. 7
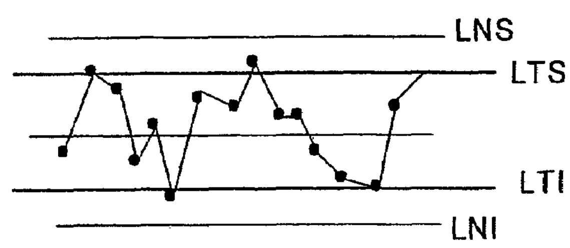
FIG. 8

PREVENTIVE DEFECT DETECTION AND CONTROL PROCESS IN COMPOSITE MATERIAL PARTS

FIELD OF THE INVENTION

The present invention refers to a preventive defect detection and control process in composite material parts carried out within the non-destructive inspection of composite material parts, and more particularly of parts used in aircraft.

BACKGROUND OF THE INVENTION

Composite materials are currently widely used in the manufacture of aircraft parts due to their excellent mechanical features.

However, since the manufacturing processes of these parts do not assure the inexistence of defects in the manufactured parts a non-destructive inspection of all the manufactured parts is required, subjecting them to ultrasonic signals to detect defects, especially porosity and delamination defects.

If any reparable defect is detected during inspection it is repaired, and a corrective action is then established in the part manufacturing process so that the defect does not re-occur. It must be taken into account that not all defects are reparable since it may occur that a defect or a group of them generate “unserviceable parts”, according to unacceptable criteria for size, occupied area or type of inspection of the area in which they are located.

When this process is individually applied to each manufactured part, the scope of the measures used in the manufacturing process is merely corrective, being impossible to prevent the high inspection and repair costs generated in the majority of manufacture.

The process in turn requires parts or areas of the parts to be inspected where the likeliness of defects may be very low, with the subsequent cost increase.

Therefore additional control and detection processes are required, and the present invention is focused on this demand.

SUMMARY OF THE INVENTION

The present invention proposes a preventive defect detection and control process within the field of non-destructive inspection of mass produced composite material parts, comprising the following steps for each manufactured part:

a) Automatically obtaining representative parameters of backwall and intermediate echo signal results from pulse-echo ultrasonic scanning in each cell of a mesh predefined on the part or predetermined areas thereof. Areas considered to be “conflictive”, where the occurrence of the defect is historically “repetitive”, will preferably be analyzed, but an overall analysis of the entire part due to the randomness of the defect location and generation, similarly occurring in historically “healthy” areas, may be of interest.

b) Storing said parameters in a database.

c) Statistically analyzing the stored parameters corresponding to a certain area of a certain part for:

c1) detecting isolated and significant alterations in the part manufacturing process generating porosity defects (overall and in layers) in the analyzed area in order to be able to perform the corresponding preventive action; or c2) detecting slow and permanent alterations in the part manufacturing process generating porosity defects (overall and in layers) in the analyzed area in order to be able to perform the corresponding preventive action; or c3) detecting areas with a negligible defect generation probability in order to identify them as areas susceptible of inspection by sampling. The inspection reduction must encompass all the defects existing in composite materials (porosity, delamination, debonding, foreign objects . . . ), a required condition for the viability of any sampling.

Therefore, the process according to the invention has a preventive purpose and a required inspection reduction purpose.

The preventive analysis is based on statistical process control by means of using control charts of the backwall echo attenuation and intermediate echo amplitude signals, which signals may be considered “key signals” due to their high occurrence and variation associated costs (repairs, HNCs . . . ).

Analysis of the required inspection reduction possibility is based on the process capability index measurement.

Other features and advantages of the present invention will be understood from the following detailed description thereof in relation to the attached figures.

DESCRIPTION OF THE DRAWINGS

FIG. 2 schematically shows the transmission of an ultrasonic signal on an inspected part.

FIG. 3 schematically shows the backwall echo amplitude, slightly attenuated with respect to the entrance one (or backwall calibrated) once the ultrasonic signal crosses through the thickness of the part in the inspected area or point.

FIG. 4 schematically shows the overall porosity and layer porosity study ranges in the preventive detection and control process according to the present invention.

FIGS. 7 and 8 show “classic” control charts of two statistical cases representing different process capability statuses, the value quantified by means of the process capability index (Cp/Cpk or Pp/Ppk) used in the detection and control process according to the present invention.

DETAILED DESCRIPTION OF THE INVENTION

Figure 1:
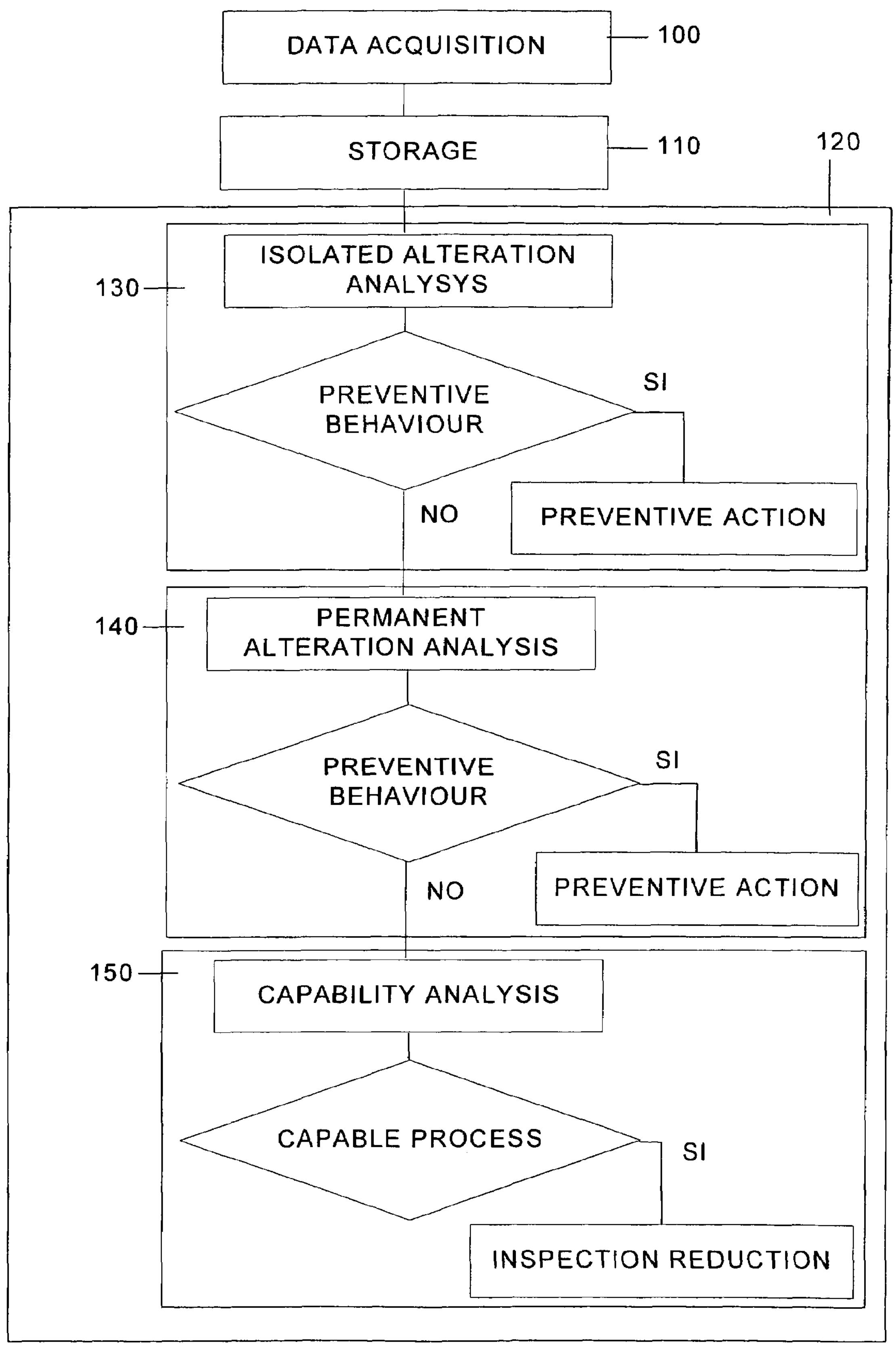
FIG. 1 shows a diagram of the preventive defect detection and control process according to the present invention.

Following the block diagram of FIG. 1, the first step 100 of the preventive defect detection and control process in composite material parts according to the present invention is automatic data acquisition.

The control variables used in the process for detecting “potentially preventive” porosity defects (overall and in layers) are the backwall echo and the intermediate echo and the values which they acquire are:

Backwall echo attenuation level expressed in dB or in % screen total height for overall porosity analysis.

The value of the intermediate echo amplitude, generally expressed as % screen total height for layer porosity analysis.

This process could likewise control any defect initially considered to be "not preventive" (delamination, foreign objects, debonding . . . ), monitoring the "standard" and "non-random" patterns associated to their ultrasonic echo variation in "classic" graphs, which is not the case in the corresponding improved sensitivity charts/Time weighted charts (since these defects are not usually preventable).

Data acquisition is carried out by means of a known machine 1 transmitting an ultrasonic signal 5 on a part 3 and capturing the bounced signal 7 along its thickness T.

The example of FIG. 3 show the ultrasonic energy U variation of the signal along thickness T of the part, and it can be seen that the backwall echo 9 is attenuated with respect to the entrance eco (or backwall calibrated), generally indicating the existence of an overall porosity defect in the part when critical attenuation values are reached (tolerance) unless there are significant intermediate echoes (which represent another type of defects) or identification of attenuation signals inherent to the process and not the defect.

The mentioned values are obtained automatically in each inspected part for one or several areas thereof, of constant thickness, subdivided into cells. Thickness uniformity in the analyzed cell allows filtering those "false" attenuations caused by guided bouncing of the ultrasonic signal in sloping areas or discontinuous changes on thickness.

The analyzed areas will be those in which the corrective study has reflected the high defect generation probability (repetitive behaviors). The entire part may also be analyzed when process randomness generates defects in historically "healthy" areas.

Each basic cell of the meshing defined by area includes the existing attenuation and intermediate echo values as the machine caliper tracks and inspects its associated area. Each inspected "point" or "basic area", usually 4 $mm^2$, corresponds to a piece of data or measurement within the cell, including more or less values according to their basic size.

The basic cell size for each analyzed area or zone with constant thickness will correspond to the software overflow—detection capability compromise, being standard practice to search for the largest sizes "possible" in the attempt to generate a "healthy" area in the cell when the defect evolves in said cell.

This practice provides the standard deviation (its classic chart) with a high detection capability for the following reasons:

The healthy and defective area combination within a single cell will cause significant alterations in the intermediate echoes or attenuation standard deviation.

The larger the sampled population (the population of attenuations and intermediate echoes contained per basic cell), the greater the capability of the standard deviation to detect special causes for process variation.

The standard deviation will thus provide an additional efficient statistical alarm due to any potential defect generation.

The process herein proposed could therefore obtain those statistically representative parameters (mean, mode, median, standard deviation and whole population) of all the values obtained in the cell.

The data acquisition step 100 can be carried out within the part inspection process aimed at determining part compliance or non-compliance as a specific action of the process according to the present invention.

The second step 110 of the process is the storage of the mentioned parameters of each cell in a database associated to a plurality of index data, such as the following:

Characteristic which the parameters correspond to (backwall echo or intermediate echo).

Cell code.

Code of the area the cell belongs to.

Data identifying the part which the area belongs to.

Data identifying relevant factors of the part manufacturing process (for example tools or machines used).

Attenuation values exceeding the maximum allowed by the "gate" chosen in the machine (window Ls in FIG. 4) will not be included in order to avoid noise, let's take for example the approximate 18 dB under an 20% gate screen height for the backwall echo, upper tolerance limit representative of the "already" generated overall porosity defect. Should there be significant attenuation or intermediate echo values not related with the defect and "assignable" to different factors such as roughness, dirt or edge effect, said data will be acquired but will not be taken into account in the subsequent statistical analysis.

Lower tolerance limits are similarly set such that the process according to the present invention is applied to predetermined ranges. In the case shown in FIG. 4, the overall porosity study range is the one indicated by the If interval, in which the represented attenuation value of the backwall echo Eb is found, not being possible to include values exceeding the limit set in the machine (gate Ls). The range If will be defined by the maximum screen height of the backwall echo when there is no attenuation (aspect generally related to initial machine calibration) and the chosen value of gate Ls which normally brings a compromise between defect detection and noise filtering.

For its part the layer porosity study range is the one indicated by interval I1, in which the value of intermediate echoes E1, E2 . . . are found, discarding those "false" values (noise or grass) filtered through the window L1. The layer porosity study range I1 is defined between window L1 and 30% screen height "already" reportable as layer porosity. Values exceeding 30% screen height are included (no upper filter) but not considered within the preventive analysis (defect has already appear)

The third step 120 of the process is the statistical analysis of all the stored data for a certain area of a certain part or a portion of the data (this is generally all the data of the area) chosen with a significant criterion (for example, only of the parts manufactured with the use of a certain machine in a certain period).

Figure 5:
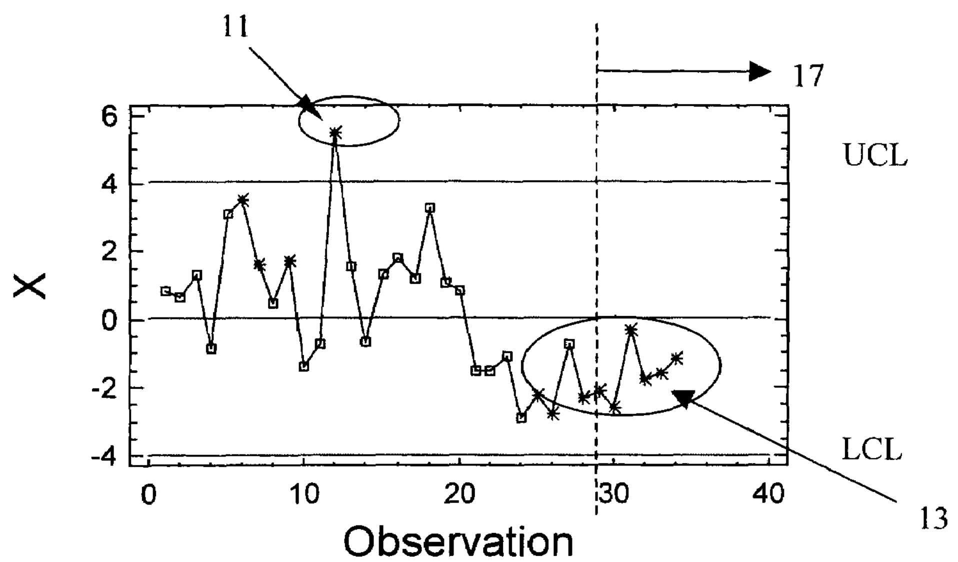
FIG. 5 shows a control chart used in the preventive detection and control process according to the present invention to analyze isolated and significant alterations.

In a first substep 130, the data of the controlled characteristic (backwall echo or intermediate echo) is analyzed in order to identify isolated and significant alterations of the part manufacturing process by means of, for example, a "classic" sample mean chart such as that shown in FIG. 5, in which one point 11 is clearly identified as being outside UCL and LCL control limits representing the natural process variability, but within the tolerance limit representative of the "already" generated defect. The identification of such alterations will give rise to the corresponding preventive action.

Figure 10:
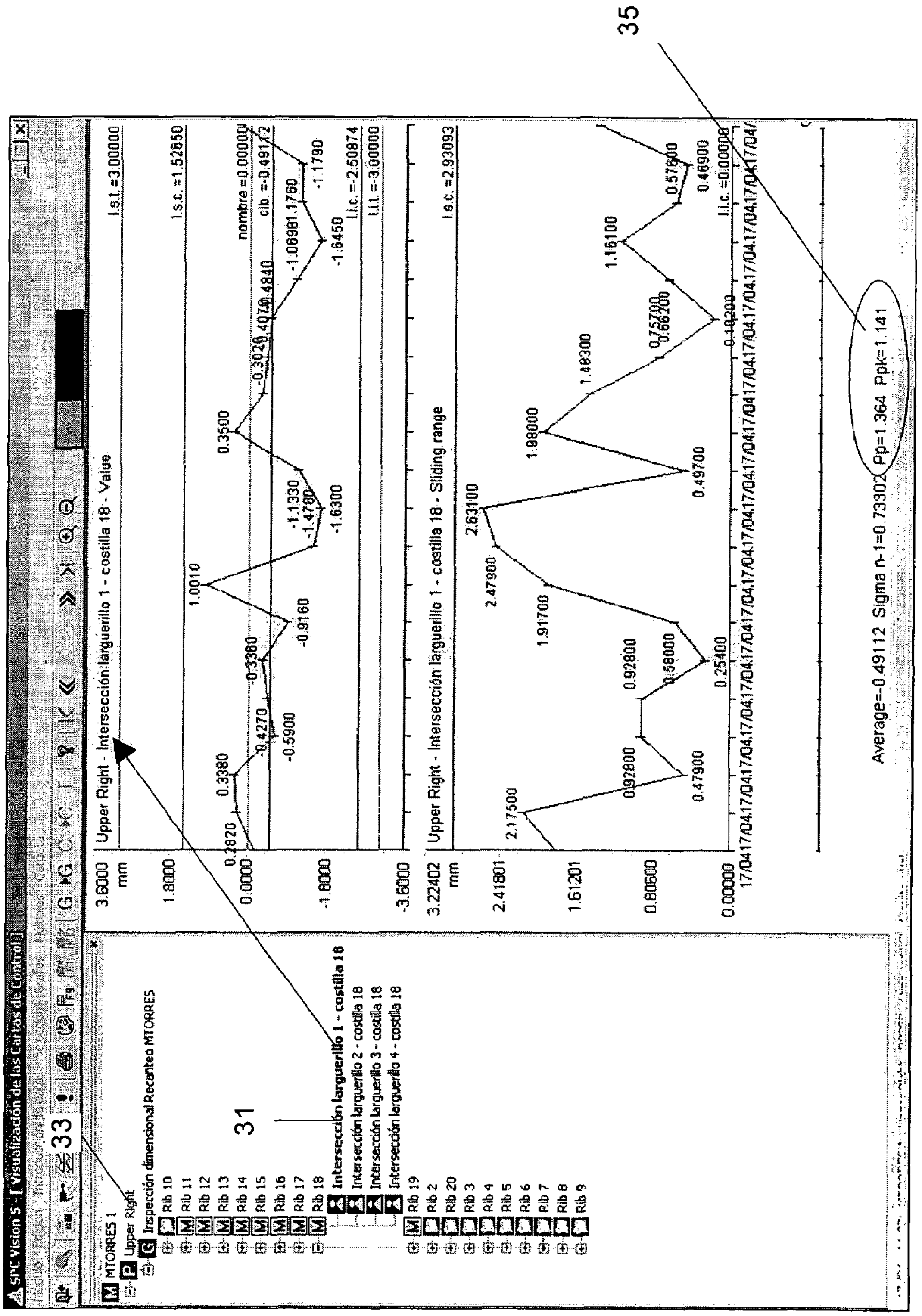
FIGS. 10-12 show computer screens with control charts such as those shown in FIGS. 5-8 corresponding to the control of “key” variables defined in “points or areas” of the part, both the variable and the zone being identified in the left portion of the screens.
Figure 11:
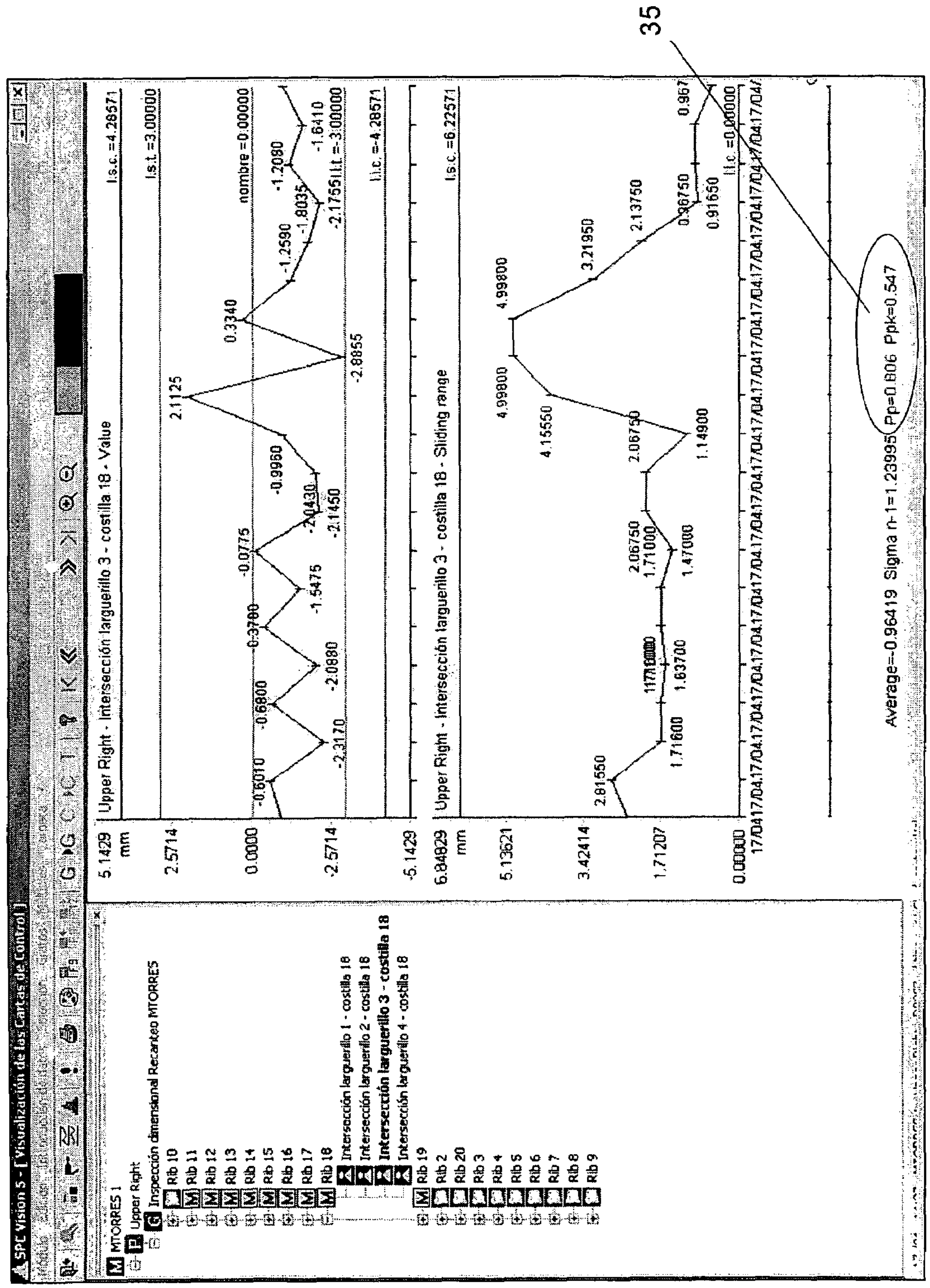

The existence of isolated and significant alterations in the scatter charts, such as, for example, the moving range charts shown in the lower part of FIGS. 10 and 11, must similarly be identified. The scatter charts are "always" analyzed together with their corresponding individual measurements (or sample mean), a set of control charts usually known as "classic" charts.

Figure 6:
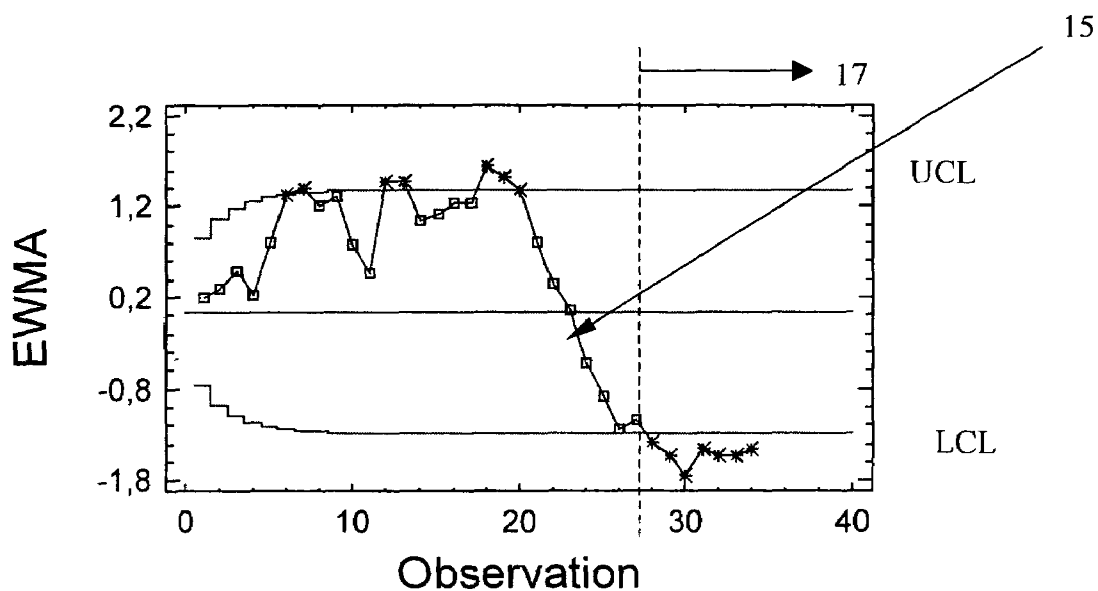
FIG. 6 shows a control chart used in the preventive detection and control process according to the present invention to analyze slow and permanent alterations in the process.

Should no isolated alteration be detected, the process continues to the substep 140 in which the data of the controlled characteristic (backwall echo or intermediate echo) is analyzed in order to identify possible slow and permanent alterations by means of, for example, a "special" improved sensitivity charts (moving average/exponentially weighted moving average), such as that shown in FIG. 6, in which a problem from subgroup 28 is detected, being able to speculate that the manufacturing process deficiencies began again in subgroup 24 (more or less trend behavior). The identification of such types of alterations will give rise to the corresponding preventive action.

Analysis of the graphs of FIGS. 5 and 6 can identify relevant process trends, such as that shown in area 15 of FIG. 6 (improved sensitivity graph), a non-random behavior also detected in its associated classic charts (FIG. 5) by means of the identification of non-random patterns in area 13 (Western Electric Rules).

Also note the identification of area 17 as a preventive action application boundary particularly after subgroup 28, the first observation out of control over the clear and decreasing trend of the improved sensitivity chart (EWMA) shown in FIG. 6.

Should no alteration be detected when having reached statistical control in both charts (classic and improved sensitivity (EWMA) graphs), the process continues to substep 150 in which the data of the controlled characteristic (backwall echo or intermediate echo) is analyzed in order to identify inspection reduction possibilities due to the low probability of the occurrence of defects. This is carried out by means of analyzing the process capability index in the analyzed meshing cells, the index being "Cp" or "Cpk" (for non-centered distributions) and calculated in normal distributions by means of the following expressions:

Centered Processes with Respect to Specification Limits:

$$Cp=\text{Specified Variability}/\text{Natural Variability}=(UTL-LTL)/6\sigma$$

Non-Centered Processes with Respect to Specification Limits:

$$Cpk=\text{smaller value of }\{Cpk_{(upper)}, Cpk_{(lower)}\},$$

where $Cpk_{(upper)}=(UTL-X)/3\sigma$ and $Cpk_{(lower)}=(X-LTL)/3\sigma$

A process characterized by "centered" distributions will be capable (FIG. 7) if its natural variability between UNL and LNL natural limits, due exclusively to random causes of the process, is lower than the variability specified by the UTL and LTL tolerance limits.

The "non-centering" of the process with respect to the tolerance interval decreases its capability value, taking this factor into account in calculating the "Cpk" index, a reference value to be analyzed in this type of distributions.

The centering of the process will also increase the Cpk index up to a maximum value equal to the Cp index. This is why the Cp index is also known as "the process potential".

In terms of capability index:

Cpk>1: Capable process

Cpk=1: Strictly capable process

Cpk<1: Non-capable process

All those cases under control in which Cpk>>1 will be susceptible of being inspected by sampling based on their negligible defect generation probability.

Figure 9:
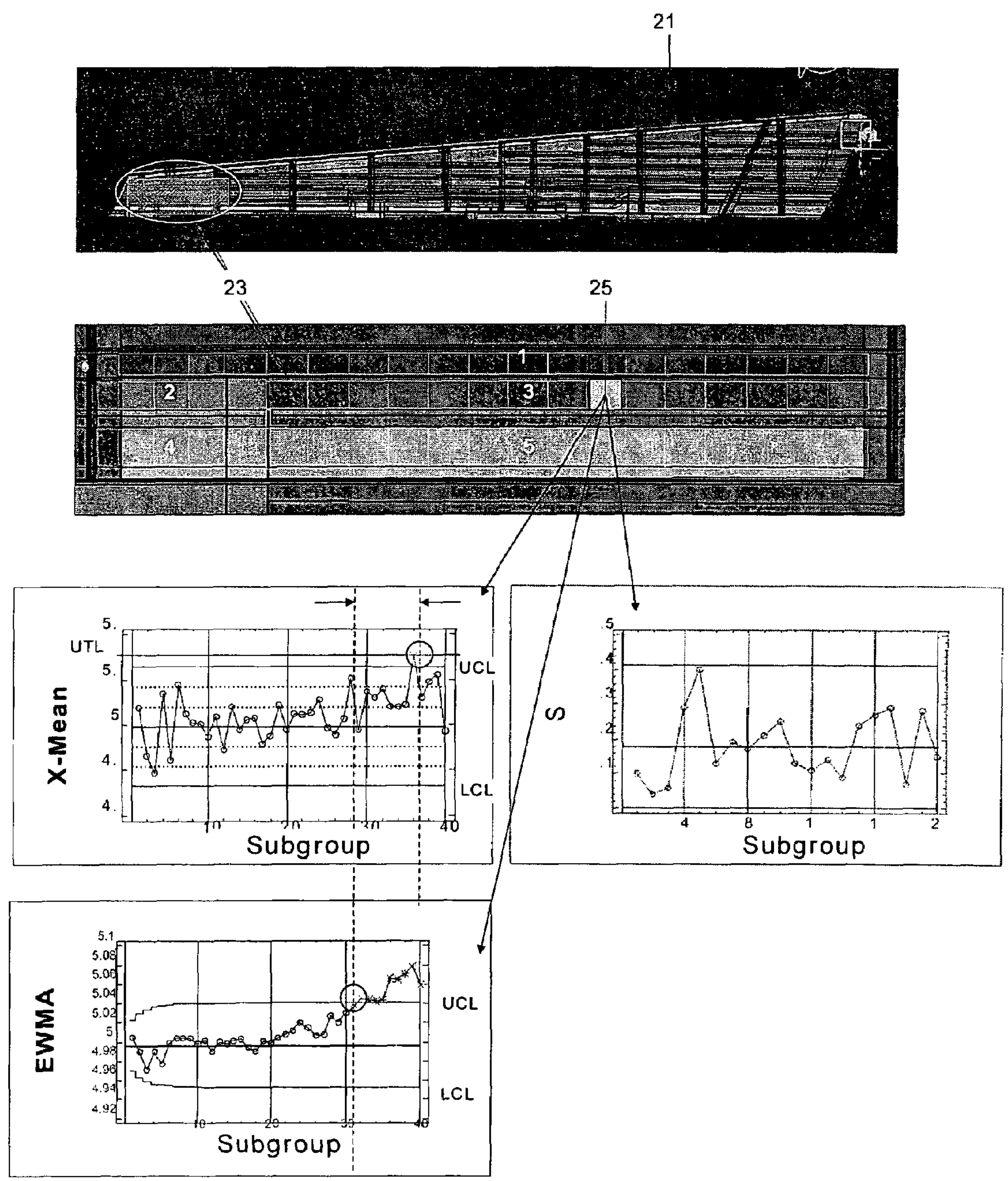
FIG. 9 shows the meshing carried out in a predetermined area of a part and sampling mean, exponentially weighted moving average and standard deviation charts corresponding to each one of the cells.

Implementation of step 120 of the process is carried out in a computer provided with suitable means for carrying out the mentioned statistical analyses with the data stored in the database after being acquired by the machine carrying out the ultrasonic scanning. As shown in FIG. 9, the statistical charts used in the analysis correspond to the data obtained by the ultrasonic scanning of cell 25, belonging to area 23 in part 21, the suitable meshing of area 23 object of study having been previously established with the aforementioned criteria. FIG. 9 shows the preventive warning of the improved sensitivity chart in performances prior to the occurrence of the defect, that is, prior to the existence of a value outside the tolerance range in the associated classic means charts.

Figure 12:
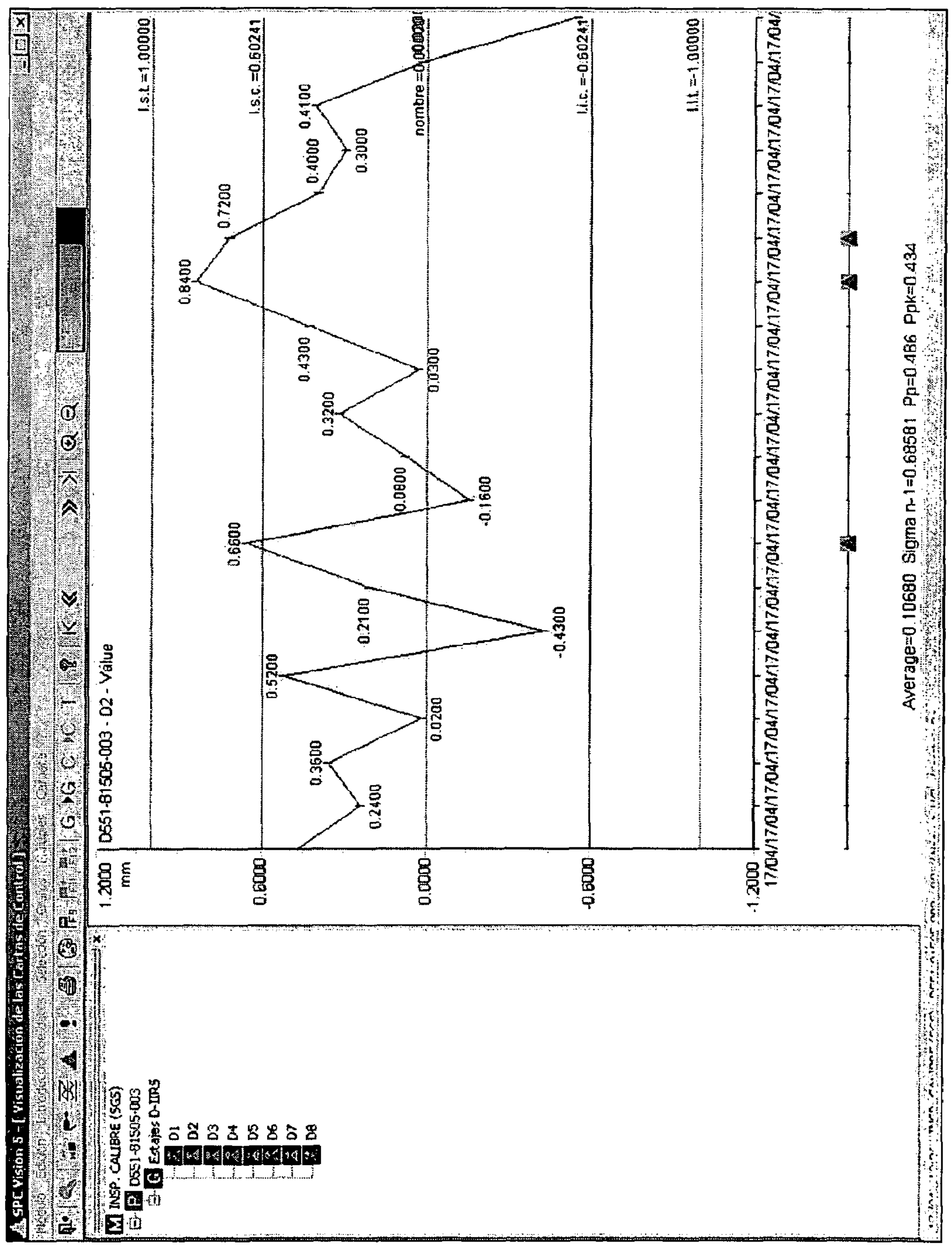

Results such as those shown in FIGS. 10 to 12 are obtained in a preferred embodiment of the process.

Shown in the right hand portion of the screen in FIGS. 10 and 11 in relation to part 33 are the control charts of the "key" characteristic 31 identified in the left hand portion of the screen, and the capability indices 35 are indicated on the lower bar. Upon analyzing their content, it can be seen that the chart of FIG. 10 represents a capable process (capability index greater than 1), whereas the chart of FIG. 11 represents a non-capable process (capability index less than 1).

FIG. 12 similarly show control a control charts of the presence of isolated and significant alterations.

Any modifications comprised within the scope defined by the following claims may be introduced in the embodiments described above.

The invention claimed is:

1. In a preventive defect detection and control process for produced aircraft-type composite material parts, the improvements comprising:

a) automatically obtaining from pulse-echo ultrasonic scanning representative parameters of backwall and intermediate echo signal results in each of at least areas of cells of a mesh predefined on the parts;

b) storing said parameters in a database; and c) statistically analyzing the stored parameters corresponding at least to certain of the areas of the cells of the parts for:

c1) detecting isolated and significant alterations in the parts manufacturing process generating porosity defects (overall and in layers) in the analyzed areas of the cells of the parts for performing corresponding first preventive action; or c2) detecting slow and permanent alterations in the part manufacturing process generating porosity defects (overall and in layers) in the analyzed areas of the cells of the parts for performing corresponding second preventive action; or c3) detecting analyzed areas of the cells of the parts with negligible defect generation probability for identifying cells of the parts susceptible of inspection by sampling.

2. A preventive defect detection and control process in composite material parts according to claim 1, characterized in that the areas of corresponding of the are of constant thickness.

3. A preventive defect detection and control process in composite material parts according to claim 1, characterized in that the analysis of step c1) is carried out by means of classic sample mean and standard deviation charts.

4. A preventive defect detection and control process in composite material parts according to claim 1, characterized in that the analysis of step c2) is carried out by means of improved sensitivity or weighted over time charts (MA/EWMA).

5. A preventive defect detection and control process in composite material parts according to claim 1, characterized in that the analysis of step c3) is carried out by means of obtaining a process capability index (Cpk).

6. A preventive defect detection and control process in composite material parts according to claim 2, characterized in that the analysis of step c1) is carried out by means of classic sample mean and standard deviation charts.

7. A preventive defect detection and control process in composite material parts according to claim 2, characterized in that the analysis of step c2) is carried out by means of improved sensitivity or weighted over time charts (MA/EWMA).

8. A preventive defect detection and control process in composite material parts according to claim 3, characterized in that the analysis of step c2) is carried out by means of improved sensitivity or weighted over time charts (MA/EWMA).

9. A preventive defect detection and control process in composite material parts according to claim 6, characterized in that the analysis of step c2) is carried out by means of improved sensitivity or weighted over time charts (MA/EWMA).

10. A preventive defect detection and control process in composite material parts according to claim 2, characterized in that the analysis of step c3) is carried out by means of obtaining a process capability index (Cpk).

11. A preventive defect detection and control process in composite material parts according to claim 3, characterized in that the analysis of step c3) is carried out by means of obtaining a process capability index (Cpk).

12. A preventive defect detection and control process in composite material parts according to claim 4, characterized in that the analysis of step c3) is carried out by means of obtaining a process capability index (Cpk).

13. A preventive defect detection and control process in composite material parts according to claim 6, characterized in that the analysis of step c3) is carried out by means of obtaining a process capability index (Cpk).

14. A preventive defect detection and control process in composite material parts according to claim 7, characterized in that the analysis of step c3) is carried out by means of obtaining a process capability index (Cpk).

15. A preventive defect detection and control process in composite material parts according to claim 8, characterized in that the analysis of step c3) is carried out by means of obtaining a process capability index (Cpk).

16. A preventive defect detection and control process in composite material parts according to claim 9, characterized in that the analysis of step c3) is carried out by means of obtaining a process capability index (Cpk).

* * * * *